United States Patent [19]

Teves

[11] Patent Number: 5,029,591
[45] Date of Patent: Jul. 9, 1991

[54] ENDOTRACHEAL CARDIAC MONITOR

[76] Inventor: Leonides Y. Teves, 623 - 39th St. West, Brandenton, Fla. 33505

[21] Appl. No.: 330,641

[22] Filed: Mar. 30, 1989

Related U.S. Application Data

[63] Continuation-in-part of Ser. No. 31,032, Mar. 26, 1987, abandoned.

[51] Int. Cl.$^5$ .............................................. A61B 5/02
[52] U.S. Cl. .................................. 128/715; 128/773; 128/207.15; 604/96
[58] Field of Search ........... 128/715, 773, 671, 207.15; 604/96

[56] References Cited

U.S. PATENT DOCUMENTS

| | | | |
|---|---|---|---|
| 541,901 | 7/1895 | Thornton | 604/96 |
| 3,731,692 | 5/1973 | Goodyear | 128/207.15 |
| 3,766,927 | 10/1973 | Jackson | 128/207.15 |
| 4,331,156 | 5/1982 | Apple et al. | 128/715 |
| 4,383,534 | 5/1983 | Peters | 128/715 |

FOREIGN PATENT DOCUMENTS 1209213 8/1986 Canada .

Primary Examiner—Lee S. Cohen
Assistant Examiner—J. P. Lacyk
Attorney, Agent, or Firm—Frijouf, Rust & Pyle

[57] ABSTRACT

A flexible endotracheal tube is disclosed for acoustically monitoring the heart sounds of a patient. The tube comprises a flexible conduit to provide a respiratory passage and a separate cardiac sound passage conduit. An inflatable cuff is disposed near the distal end of the flexible conduit to contact and sealingly conform to the interior wall of the trachea upon inflation. The closed chamber of the inflatable cuff is in fluid communication with the separate sound passage for enhanced acoustic reception from the inflatable cuff. The distal end of the sound passage conduit includes a terminal end defining an angular cut to enhance the acoustic reception of the heart sounds acoustically transmitted from the interior tracheal wall through the inflatable cuff and into the acoustically separate conduit. The sound conduit extends longitudinally with the respiratory conduit and is constructed within an enlarged wall forming one side of the respiratory conduit to provide a figure eight configuration in cross section such that the two conduits mean are acoustically separate from each other but contained within the same endotracheal tube. A means for permitting the pressurizing of the sound conduit and a means for permitting the monitoring of pressure variations within the conduit is also disclosed.

11 Claims, 4 Drawing Sheets

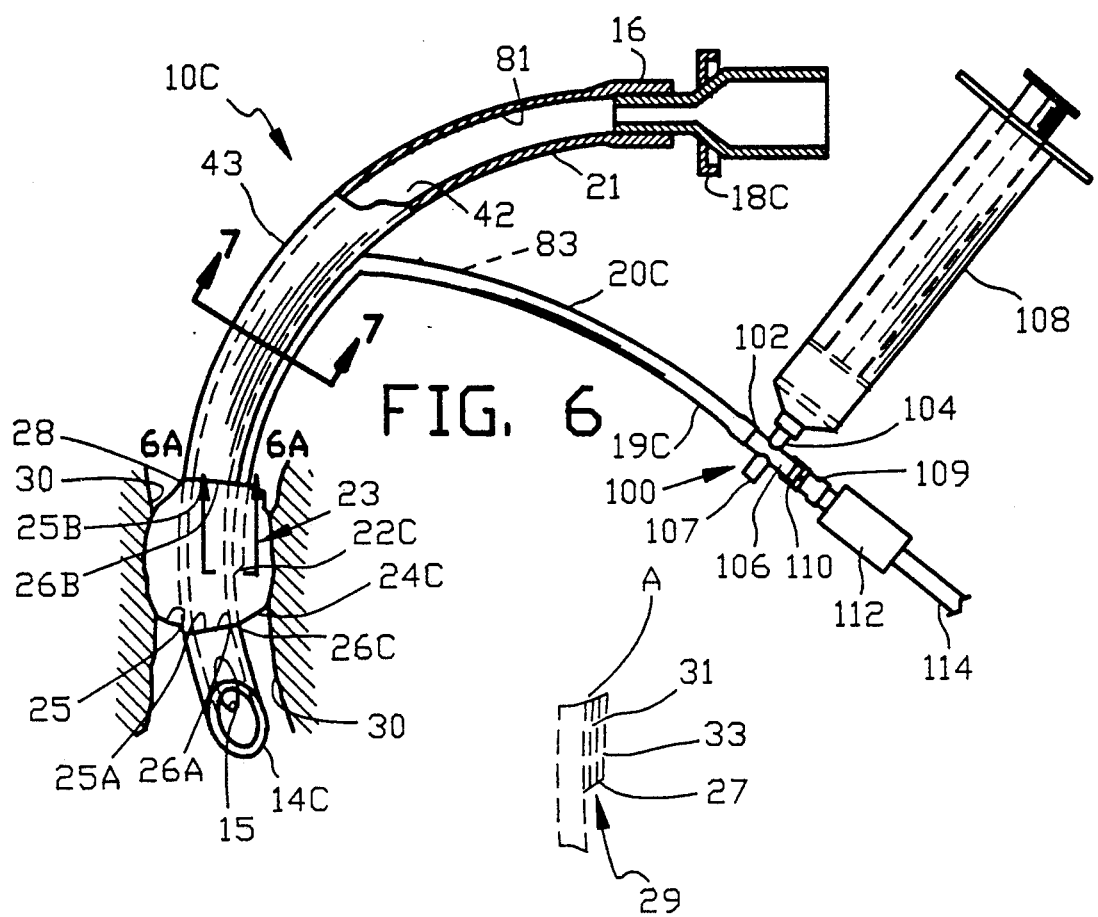
FIG. 6
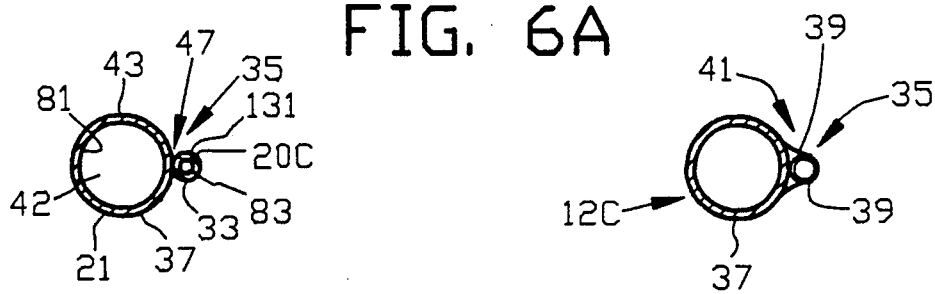
FIG. 6A
FIG. 7
FIG. 8
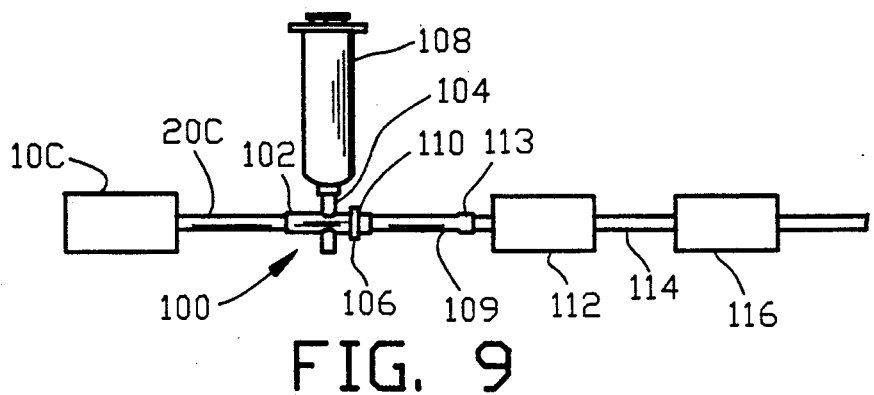
FIG. 9

5,029,591

ENDOTRACHEAL CARDIAC MONITOR

CROSS-REFERENCE TO RELATED APPLICATION

This application is a continuation-in-part of Ser. No. 031,032 filed Mar. 26, 1987, now abandoned which is incorporated by reference as if fully set forth herein.

BACKGROUND OF THE INVENTION

1. Field of the Invention

This invention relates to an apparatus for improved acoustic monitoring of the cardiac pulse while simultaneously administering anesthetic gases to a patient during surgery.

2. Description of the Prior Art

During operations in which general anesthesia is used, the accepted practice is to administer the anesthetic gases through a flexible endotracheal tube which is inserted through the mouth of the patient and into the trachea. The early, rudimentary versions of such an endotracheal tube were greatly improved by the addition of sealing means at the outside of the distal end of the tube. The sealing means in most common usage today comprises an inflatable cuff which can expand into contact with the interior wall of the trachea. With trachea thus blocked, positive control over the administration of anesthesia and of the respiration itself is permitted through the respiratory passage in the endotracheal tube.

The administration of anesthesia gases tends to produce a state of relaxation of muscle tissue. This effect is quite desirable to the surgeon who must cut into and through such tissue, but it also can have effects which are not desired. Although some of the undesired effects may not be evident until the post-operative recovery period, the possibility of cardiac arrest is typically of utmost concern during the surgery itself.

Since cardiac arrest is an ever-present danger during the condition of general anesthesia, the cardiac pulse must be monitored carefully and continually. In fact, in some states there exists practically an absolute requirement to monitor the actual heart sounds during surgical procedures. In other areas, the amount and type of cardiac monitoring is left to local or hospital rule, or to the preference of the anesthesiologist. Sometimes, such monitoring is accomplished acoustically as by taping an acoustic stethoscope pickup directly to the exterior of the body of the patient in the region of the chest. Such cardiac monitoring is perhaps more often accomplished by electrical or electronic means which essentially monitor motor nerve impulses. The electrical activity thus picked up is usually converted into audible "beeps" which essentially serve only to monitor the heart rate, and occasionally the same electrical activity may be presented for visual observation on an oscilloscope. This direct technique of electrical monitoring of motor nerve impulses is often remarkably less sensitive than acoustic monitoring of the cardiac pulse, and in addition the audible "beeps" produced by electrical monitoring are far less informative of the actual activity and condition of the heart than the true heart sounds available through acoustic monitors. By listening to the actual heart sounds through acoustic monitoring means the anesthesiologist can receive the earliest possible indication that the heart is becoming depressed due to the anesthetic, thus permitting the anesthesiologist to take early and minimal corrective measures so that there is little or no impact on the progress of the surgical procedure and no adverse effect on the patient.

Acoustic monitoring of the heart during surgery has been accomplished by using one or more acoustic pickups for stethoscopes taped to the chest of the patient. However, even under the best of conditions, the heart sounds are attenuated substantially by the body tissue in the sound path from the heart to the acoustic pickup, and it is often impossible to change the location of the stethoscope acoustic pickup once the surgical procedure has begun. This type of acoustic monitoring on the outside of the chest wall is particularly difficult and unsatisfactory for obese patients, since the excessive amount of body tissue in the sound path between the heart and the acoustic pickup often attenuates the heart sounds to an unusable level.

Although the present invention is generally oriented toward cardiac monitoring during surgery, is also applicable to the carefully monitoring of the cardiac pulse which may also be required for several days after surgery while the patient is in the intensive care unit. Endotracheal monitors are well suited to such prolonged use.

The nature of the surgery permitting, one of the preferred cardiac pulse monitoring methods requires the use of a device known as an "esophageal tube", which, as its name implies, is inserted in the esophagus of the patient. Acoustic or electric sensors may be disposed near the distal end of the esophageal tube to pick up and transmit the cardiac pulse from the surrounding tissue. Unfortunately, the amount of various body fluids in the esophagus can vary drastically during the course of surgery; such variations not only can affect the ability to monitor the cardiac pulse acoustically, but can also create confusing and distracting noise. The esophageal tube itself must be sealed at its distal end in order to prevent the entrance of body fluids which may occasionally be present in the esophagus during surgery. Also, sensors located in the esophagus cannot always be positioned as close to the heart as is possible with sensors located at the distal end of an endotracheal tube. Thus esophageal sensors tend to distort the cardiac pulse. A more reliable means of monitoring the cardiac pulse with greater fidelity is desirable.

The esophageal tube has the disadvantage of being difficult to locate properly in some situations. In attempting to properly place the esophageal tube, it is possible for the anesthesiologist to perforate the wall of the esophagus resulting in "false passage". Such false passage is more likely to occur where there is scar tissue in the esophagus or where there is a congenital pouch in the wall of the esophagus which leads the probing tip of the esophageal tube in the wrong direction. Due to the nature of the tissue involved, false passage is a less significant problem in the trachea than in the esophagus. Since an endotracheal tube is used in most cases for the administration of the anesthetic gases, the use of a separate esophageal tube merely for the purpose of monitoring the cardiac pulse creates excessive and unnecessary crowding in the area of the mouth of the patient, and adds unnecessary expense to the surgical procedure itself. Also certain forms of radical neck surgery involving the esophagus would necessarily preclude the use of an esophageal stethoscope in any form.

Even where esophageal stethoscopes are used routinely, it is difficult to adequately seal the esophagus to prevent fluids from the digestive track from moving toward the mouth of the patient during the operation. Depending somewhat upon the nature of the surgery and the length of the operation, these fluids may find their way into the trachea of the patient, and ultimately into the lungs of the patient. Such leakage of fluids from the esophagus into the trachea can cause aspiration pneumonia, which is a problem commonly associated with the use of esophageal stethoscope tubes.

Current monitoring devices which convert sound into an electrical signal for transmission to the output means are generally deficient in two respects. First, the output is often limited to a series of gated tone bursts commonly known as "beeps". Such a signal provides only an indication of the cardiac rate, and actually serves to conceal the degree of depression of the heart during surgery. In those systems where additional information containing more of the actual heart sound is used, the deficiency arises from the fact that the output is generally available only to the anesthesiologist, and not to the surgeon(s) operating on the patient.

Thus, it is desirable to monitor the heart sounds acoustically via a trachea tube. However, these heart sounds must be transmitted via an axial canal separate from the respiratory canal. When this is attempted, however, several major problems occur. One such problem is the amount of space available in a patient's trachea. The tracheal tube must have a relatively large opening passage in order to provide enough air to the patient and thus tube uses much of the space available in the patient's trachea. In addition, since the respiratory tube is sealed at its distal end, the second acoustical tube would be blocked by the seal. Also, if two tubes were to be used they could rub on each other causing extra sounds and confusion. Another mechanical problem is the placement of the two tubes. The large respiratory tube is relatively easy to insert. The smaller acoustical tube, however, would tend to wander around and be relatively uncontrollable.

Thus, the solution is directed to a combination of the two tubes into one tube. This, in turn, has several problems. As discussed, the main respiratory tube canal must have a relatively large diameter in order to control the respiratory process. The wall thickness around the canal must be pliable enough to conform to the trachea passage. This argues for a thin walled tube. The outside wall must be smooth for easy and unobstructed passage. On the other hand, the acoustic canal must be large enough to allow acoustic wave forms to pass unmodulated so that enough sound energy can pass from the patient to avoid sound tapes. In addition, the two canals must be acoustically separate.

Therefore, it is an object of this invention to provide an apparatus which overcomes the aforementioned inadequacies of the prior art devices and provides a significant improvement to the advancement of the prior art.

Another object of this invention is to provide a flexible endotracheal tube with an inflatable cuff suitable for sealing the trachea and having means for permitting the monitoring of pressure variations within the inflated cuff.

Another object of this invention is to provide a dual canal tracheal tube constructed to conform to the tracheal passage allowing a maximum opening for both canals while still providing acoustical separation and a smooth, no crevice, outside perimeter.

Another object of this invention is to provide a flexible conduit to conduct pressure variations from an inflatable cuff on the distal end of an endotracheal tube to an external monitor connector.

Another object of this invention is to provide a diaphragm-sealed connected in the pressurization conduit system of an endotracheal tube having an inflatable cuff so that sounds transmitted through the tracheal wall to the inflated cuff may be monitored externally while maintaining the pressure integrity of the inflated cuff and conduit system.

Another object of this invention is to provide an endotracheal cardiac monitor so that only one tube is required to be inserted into the mouth of a patient during surgery thus reducing crowding in the vicinity of the mouth of the patient as well as reducing the expense of equipment required for surgery.

Another object of this invention is to provide an electromechanical transducer to convert the pressure variations representing heart sounds into an electrical signal suitable for processing and specific distribution.

Another object of this invention is to provide an output means wherein the electrical signal representing the heart sounds is displayed on a video display and on a chart recorder, as well as being made available as an audio output either to headphones or to a loudspeaker.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purposes of summarizing the invention, the invention comprises an apparatus which permits the administration of anesthetic gases to a patient during surgery through the use of an endotracheal tube which simultaneously permits the acoustic monitoring of the cardiac pulse at a location in the trachea close to the heart. The invention comprises a flexible endotracheal tube, typically made of polyvinylchloride or similar plastic, which terminates at its proximal end in a standard fitting compatible with anesthesia machines. The distal end of the endotracheal tube is open, and a respiratory passage within the endotracheal tube provides fluid communication between the anesthesia machine and the patient's trachea.

Disposed near the distal end of the endotracheal tube is an inflatable cuff. In use, the endotracheal tube is typically inserted while the cuff is deflated. The cuff is adapted so that when it is inflated, it expands and comes into contact with the inner wall of the trachea. Not only does this serve to gently center the distal end of the endotracheal tube so as to minimize irritation of the trachea of the patient, but it also serves to seal the trachea, thus providing positive control over the administration of anesthetic gases and of the respiration process of the patient during surgery.

Inflation of the inflatable cuff is accomplished through a separate conduit which is in fluid communication with the interior of the inflatable cuff. Near its proximal end, the inflation conduit branches into two other conduits, both of which are in fluid communication with one another and therefore, with the interior of the inflatable cuff. The proximal end of the first branch of the inflation conduit terminates in an inflation connector through which the fluid is initially pumped to pressurize the conduit and thereby inflate the cuff. This inflation connector often contains a valve means such as a spring loaded check valve to preserve the pressure integrity of the conduit and inflatable cuff system.

The second branch at the proximal end of the conduit terminates in a monitor connector. This connector includes a sealing diaphragm which serves to preserve the pressure integrity of the cuff inflation system while simultaneously permitting acoustic energy in the form of cardiac pulses to be transmitted out of the apparatus and into the desired monitoring device.

The acoustic energy of the cardiac pulse is sensed by an electromechanical transducer such as a piezo electric microphone housed within a transducer connector mated with the monitor connector. The transducer converts the sound energy into an electrical signal which is used to drive the output means comprising, in general, a signal processor, a visual display, a chart recorder and one or more forms of audio output.

The inflation conduit is formed in a side wall which defines the main endotracheal tube conduit or canal. The wall is expanded slightly in one section and the inflation conduit is constructed in this expanded side wall. The main conduit can be constructed to be elliptical to give added area if desired. The expanded side wall results in a smooth outer circumference of the endotracheal tube to allow for easy insertion and removal of the endotracheal tube into and out of the patient's trachea.

An opening is formed in the outer side wall of the endotracheal tube at the distal end, the opening extending into the inflation conduit and being centered within the inflatable cuff so that air or fluid flowing in the inflation conduit will expand the cuff.

The invention may further be embodied in an apparatus and method of use comprising a flexible endotracheal tube for insertion through a an opening to a patient's respiratory system and into the trachea of the patient for acoustically monitoring actual heart sounds of the patient and supplying life supporting and anesthetic gases to the patient. The flexible endotracheal tube comprises a flexible conduit having a proximal end and a distal end with an axial bore extending from the proximal end to the distal end to provide a respiratory passage for the administration of life supporting and anesthetic gases to the patient and for the control and monitoring of respiration of the patient during surgery. The flexible conduit includes an internal and an external surface. A second conduit having a proximal and a distal end with an axial bore extending therebetween extends longitudinally between the two surfaces of the flexible conduit. The first conduit is formed as a structure that is acoustically separate from the second conduit to thereby enhance the isolation of the heart sounds from the sounds of breathed air and anesthetic gases passing through the first conduit which defines the respiratory passage. An inflatable cuff having a first end and a second end is taught. The first end of the inflatable cuff is positioned proximate the distal end of the first flexible conduit and hermetically sealed to the periphery of the first flexible conduit. The second end of the inflatable cuff is hermetically sealed to the periphery of the outer surface of the conduit to form a closed chamber. When pressurized in use the inflatable cuff must be large enough to contact and sealingly conform to the interior wall of the trachea. The distal end of the second conduit is in fluid communication with the closed chamber of the inflatable cuff to permit fluid communication with the closed chamber of the inflatable cuff and the second conduit when pressurized. The distal end of the second conduit extends midway into the closed chamber of the inflatable cuff for enhanced acoustic reception from the inflatable cuff. The distal end of the second conduit includes a terminal end defining an angular cut to enhance the acoustic reception of the heart sounds acoustically transmitted from the interior tracheal wall through the inflatable cuff and into the closed chamber and into the acoustically separate second conduit. A means for permitting the pressurizing of the second conduit and a means for permitting the monitoring of pressure variations within the second conduit is disclosed.

In a specific embodiment of the invention the inside diameter or bore of the second conduit and the three-way valve, including the bore through the valve means, are substantially the same. The internal diameter of the tube connecting the transducer to the three-way valve is substantially the same as the bore of the three-way valve and the diameter of the nipple of the transducer. This enables a direct and fluid tight connection between the second conduit, the three-way valve and the tube connecting the transducer to the three-way valve without a substantial change in internal bore size between the connections to permit unobstructed acoustic transmission therethrough. Preferably, the internal diameter is otherwise about 2.6 mm.

Preferably, the flexible endotracheal tube comprises a first conduit including a proximal end and a distal end. The first conduit includes an axial bore extending from the proximal end to the distal end to provide a respiratory passage for the administration of life supporting and anesthetic gases to the patient and for the control and monitoring of respiration of the patient during surgery. The first conduit includes a proximal end and a distal end. An inflatable cuff is disposed near the distal end of the first conduit and is large enough to contact and conform to the interior wall of the trachea with a low inflation pressure. The first conduit includes an internal surface and an external surface. The inflatable cuff includes a first end and a second end with the first end being positioned proximate the distal end of the first tube. Each of the first and second ends of the inflatable cuff are hermetically sealed to the external surface of the flexible conduit. A second conduit includes a proximal end and a distal end and is constructed in a side wall defining the first conduit. The inflatable cuff is made of a soft and pliable plastic to enable enhanced conformance of the inflatable cuff to the wall of the trachea and to enable the inflation of the inflatable cuff at a low pressure while maintaining good sound connection with minimum irritation to the trachea.

The second conduit includes an axial bore extending from the proximal end to the distal end with the distal end of the second conduit in fluid communication with the inflatable cuff to permit fluid communication with the interior of the inflatable cuff. The bore of the first flexible conduit and the bore of the second flexible conduit have a ratio of about 3.5:1. This ratio allows the first conduit to carry sufficient air for the patient, while also allowing the second conduit to carry acoustical signals with minimum attenuation. The second conduit is formed in a widened portion of the side wall of the first conduit, thus allowing the first conduit to be formed as a structure that is acoustically separate from the second conduit to thereby enhance the isolation of the heart sounds from the sounds of breathed air and anesthetic gases passing through the first conduit which defines the respiratory passage. The increased diameter of the widened portion of the conduit is less than the diameter of the second conduit, thereby allowing both canals to have the proper size for their respective functions without interference between them. A means for permitting the pressurizing of the second conduit and a means for permitting the monitoring of pressure variations within the second conduit means is also disclosed.

A method supplying life supporting and anesthetic gases to be passed to a patient's trachea while simultaneously monitoring cardiac sounds acoustically separate from a conduit supplying the supporting and anesthetic gases and the sounds associated therewith is disclosed. The method comprises providing an endotracheal tube including a first conduit having a proximal end and a distal end with the first conduit having an axial bore extending from the proximal end to the distal end to provide a respiratory passage for the administration of life supporting and anesthetic gases to the patient and for the control and monitoring of respiration of the patient during surgery. The first conduit includes a proximal end and a distal end with an inflatable cuff disposed near the distal end of the first conduit. The inflatable cuff is constructed to be large enough to contact and conform to the interior wall of the trachea with only a low inflation pressure. The first conduit includes an internal surface and an external surface with the inflatable cuff having a first end and a second end. The first end of the inflatable cuff is positioned proximate the distal end of the first tube. Each of the first and second ends of the inflatable cuff are hermetically sealed to the external surface of the flexible conduit. The second conduit includes a proximal and a distal end, with an axial bore extending therebetween and is constructed in a side wall defining the first conduit. The second end of the second conduit is in fluid communication with the inflatable cuff to permit fluid communication with the interior of the inflatable cuff. The second conduit is formed in a widened portion of the side wall of the first conduit thus enabling the first conduit to be formed as a structure that is acoustically separate from the second conduit thereby enhancing the isolation of the heart sounds from the sounds of breathed air and anesthetic gases passing through the first conduit which defines the respiratory passage. A means for permitting the pressurizing of the second conduit and a means for permitting the monitoring of pressure variations within the second flexible conduit means is disclosed.

Monitoring of heart sounds comprises inserting the distal end of the endotracheal tube within a patient's trachea in a manner to permit respiration to continue with the exchange of life supporting gases and anesthetic gases. The inflatable cuff is inflated to a low pressure such that the cuff sealingly contacts the mucous membrane of the patient's trachea. The heart sounds are acoustically transmitted from the interior tracheal wall through the inflatable cuff and into the acoustically separate second flexible conduit which terminates in a monitor connector suitable for monitoring the cardiac sounds.

In use, the inflatable cuff is pressurized or expanded by a fluid, either gaseous or liquid, after the endotracheal tube is inserted into the patient to the desired depth. When the inflatable cuff contacts and conforms to the inner wall of the trachea, it also acoustically couples the cardiac pulse from the surrounding tissue which is in close proximity to the heart and permits the propagation of the acoustic cardiac pulse through the fluid inflating medium. The propagation of that acoustic energy is guided through the flexible conduit until it reaches the monitor connector, where it is available for monitoring by the desired device.

The flexible conduits presently used for pressurization and conduction of heart sounds typically have internal diameters on the order of about one millimeter. The second conduit for pressurization and conduction of heart sounds used in this apparatus preferably has an internal diameter of about 2.16 mm in order to transmit the heart sounds with a minimum of attenuation of the acoustic energy. The use of a bore of 2.16 mm enables the direct connection of the proximal end of the second flexible conduit to a three-way valve having substantially the same bore. The transducer is directly connected, i.e., no diaphragm, to the three-way valve by a tube having an internal diameter or bore of about 2.16 mm to enable a fluid tight fit with the three-way valve and the transducer. The first conduit has a diameter of approximately 7.4 mm.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 6 is an elevational view of the second embodiment of an endotracheal tube showing the cuff inflated within the trachea;

FIG. 6A is an enlarged view taken on line 6A—6A of FIG. 6;

FIG. 7 is a sectional view of the endotracheal tube of FIG. 6 taken on the line 7—7;

FIG. 8 is sectional view of the endotracheal tube showing another embodiment;

FIG. 9 is a schematic view of the transducer directly connected to a port of a three-way valve;

FIG. 12 shows in more detail the dual conduit endotracheal monitor.

Similar reference characters refer to similar parts throughout the several views of the drawings.

DETAILED DESCRIPTION

Figure 1:
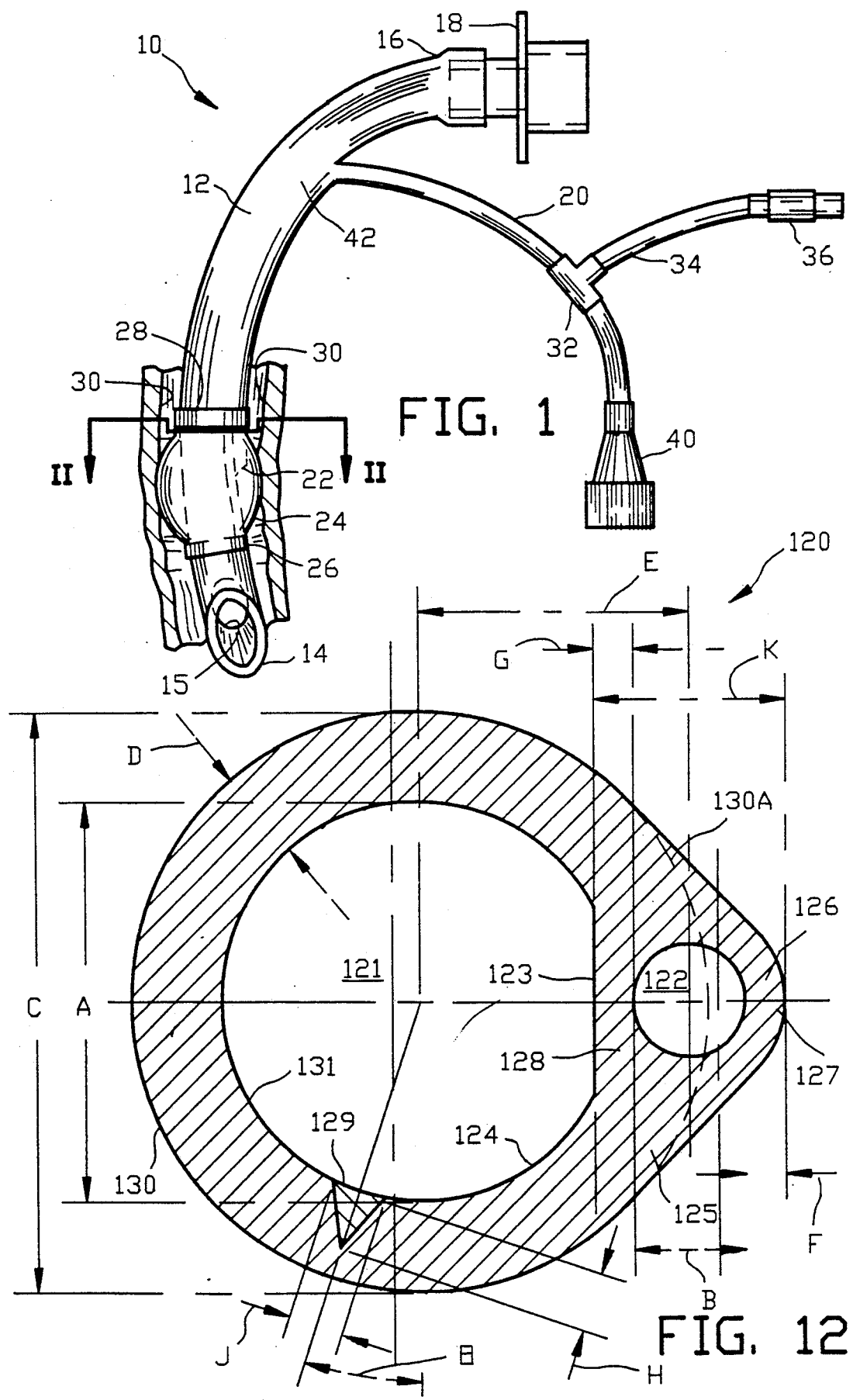
FIG. 1 is an elevational view of a first embodiment of an endotracheal tube showing the cuff inflated within the trachea.

FIG. 1 is an elevational view of the endotracheal cardiac monitor 10 in which the predominant structure is a hollow, flexible tube 12 constructed of polyvinylchloride or similar material. The tube is open at its distal end 14, which is often bias-cut as shown in FIG. 1. An aperture 15 is located in the wall of tube 12 on the side opposite the bias cut at the distal end of tube 12 in order to preclude accidental blockage of tube 12 after insertion into the trachea of a patient. The proximal end 16 of the endotracheal tube 12 is attached by friction, welding, adhesive or similar means to a rigid anesthetic connector 18 which permits connection to an anesthesia machine (not shown). Attached to the side of the endotracheal tube 12 from near the distal end 14 of said tube and running along said tube for most of its length is another, smaller flexible conduit 20. In some embodiments, this conduit 20 may be extruded integrally with the wall of the tube 12. The distal end 22 of the conduit 20 is located proximally of the distal end 14 of tube 12.

An inflatable sleeve or cuff 24 made of material such as latex, completely surrounds the distal end 14 of endotracheal tube 12. The distal end 26 of the inflatable cuff 24 is attached and hermetically sealed to the outer circumference of the distal end of endotracheal tube 12. Similarly, the proximal end 28 of the cuff 24 is attached and hermetically sealed to the periphery of the endotracheal tube 12 and conduit 20. The distal end 22 of conduit 20 is located between the distal end 26 and the proximal end 28 of cuff 24. Conduit 20 is hollow and the distal end 22 of conduit 20 is open and in communication with the volume enclosed by inflatable cuff 24.

As shown in FIG. 1, the flexible cuff 24 is inflated and has expanded to contact and conform to the inside of the trachea wall 30.

The proximal end 19 of hollow conduit 20 terminates in a standard tee fitting 32. Other embodiments of this connector, such as a Y connector, may also be used. The tee connector 32 is attached to and communications with another hollow conduit 34, the proximal end of which terminates in the inflation connector 36 which may contain valve means such as a spring-loaded check valve, not shown in the drawings. Tee connector 32 is also attached to and communicates with another hollow conduit 38 which terminates in monitor connector 40.

Figure 2:
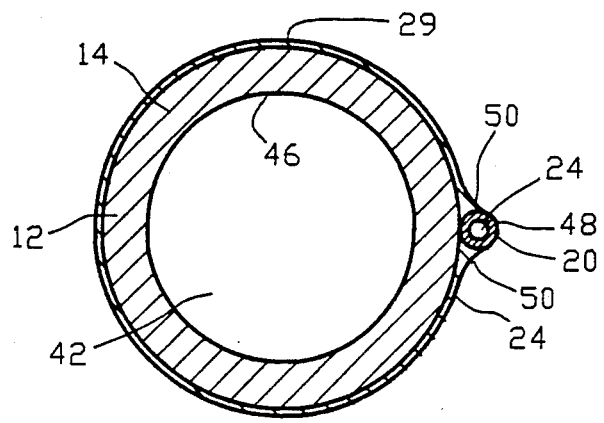
FIG. 2 is an enlarged cross-sectional view of the endotracheal tube taken on the line 2—2 of FIG. 1.

FIG. 2 is a cross-sectional view of endotracheal tube 12 taken along lines 2—2 as indicated in FIG. 1. The inner surface 46 of endotracheal tube 12 defines respiratory passage 42. The relatively thick wall of endotracheal tube 12 has an outer surface 44 to which is attached the inflatable cuff 24. As shown in FIG. 2, conduit 20 is also a tube containing pressurization passage 48. Adhesive fillets 50 are depicted in FIG. 2 as the means for attaching conduit 20 to endotracheal tube 12. Other means may also be used, or the conduit may be integrally formed with tube 12. The inflatable cuff 24 is attached to the adhesive fillets 50 and conduit 20 as well as to the outer surface 44 of endotracheal tube 12 in such a manner as to form a hermetic seal.

Figure 3:
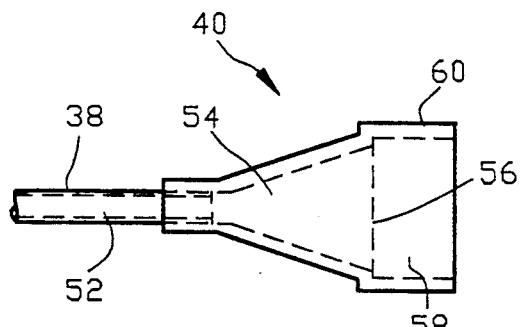
FIG. 3 is an enlarged sectional view of the monitor connector depicted in FIG. 1.

FIG. 3 shows a sectional view of monitor connector 40 which is located on the proximal end of hollow conduit 38, the distal end of which is connected to tee connector 32. The hollow interior of conduit 20 communicates with that of conduit 34 connected to the inflation connector 36 as well as to the sound passage 52 within conduit 38. Inside monitor connector 40, internal sound passage 54 expands until it terminates at diaphragm 56, which serves to maintain the pressure integrity of conduits 20, 34 and 38 as well as cuff 24 while transmitting sound from sound passages 52 and 54 to sound passage 58. Monitor connector 40 terminates in a surface 60 suitable for connection to a stethoscope or other device such as a microphone and amplifier for the purpose of monitoring acoustically or visually (as on an oscilloscope) the sound pulses from within the sound conduit.

Figure 4:
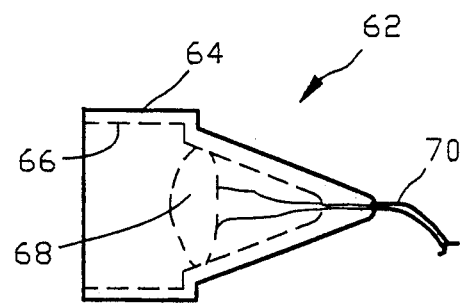
FIG. 4 is an enlarged sectional view of the transducer connector.

FIG. 4 is a sectional view of the transducer connector generally denoted as 62. Transducer connector 62 comprises a housing 64, typically made of plastic or similar material, and is shaped to mate with monitor connector 40. In the embodiment depicted in FIG. 4, inner surface 66 of connector housing 64 is intended to fit snugly about the outer surface 60 of monitor connector 40 to permit the joining of monitor connector 40 and transducer connector 62 and to retain that connection during use of the system. Transducer connector 62 contains an electromechanical transducer 68 such as a piezo electric microphone which generates an electric signal which is a function of the sound (pressure variations) within sound passage 58 in monitor connector 40. The electrical signal is transmitted by line 70 to the desired output means.

Figure 5:
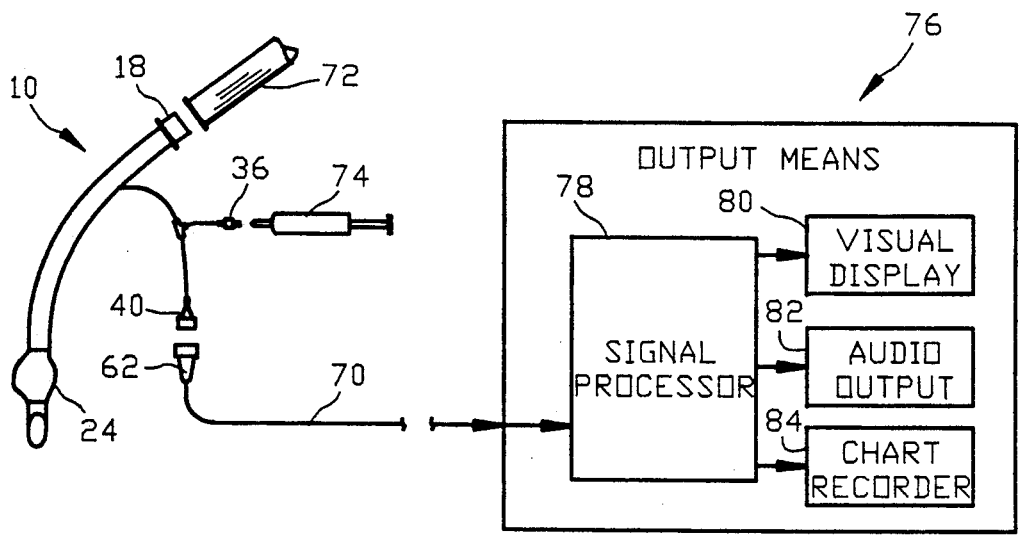
FIG. 5 is a partially exploded block diagram of the endotracheal tube and connecting devices including the output means.

FIG. 5 is a partially exploded block diagram of the entire endotracheal cardiac monitor system, including the endotracheal tube 10 and the output means 76. The proximal end of endotracheal tube 10 includes the anesthetic connector 18 which can be connected to anesthetic tube 72 which communicates with the anesthesia machine (not shown). Inflation of cuff 24 is accomplished by pressurization through inflation connector 36. This inflation or pressurization is accomplished by pressurization means 74, depicted as a simple syringe in FIG. 5. Monitor connector 40 mates with transducer connector 62 as described in the preceding paragraph. The electrical signal produced by the transducer housed within transducer connector 62 is transmitted by means of line 70 to the output means generally denoted as 76. Output means 76 generally comprises a signal processor 78 which performs such functions as filtering, amplification, and impedance matching. The output of signal processor 78 is used to drive visual display 80, and to provide outputs to audio output means 82 and the chart recorder 84. Although output means 76 is shown as a single unit in FIG. 5, it will be appreciated by those skilled in the art that the various functions depicted may be accomplished by separate units as well as by a single unit, as is well known in the art.

The character references of FIGS. 1–5 refer to similar positions in FIGS. 6–9, with the addition of the letter "C". FIG. 6 is an elevational view of another embodiment of an endotracheal cardiac monitor 10C comprising a first flexible conduit 21 and a second flexible conduit 20C. The first flexible conduit 21 includes an axial bore 81 extending from its proximal 16 to its distal end 14C to enable fluid passage therethrough. In a like manner, the second flexible conduit includes an axial bore 83 extending from its proximal end 19C to its distal end 22C to enable fluid passage therethrough. The first flexible conduit 21 is open at its distal end 14C, which is bias-cut as shown in FIG. 6. An aperture 15 is located in the wall of first flexible conduit 21 to prevent accidental blockage of the first flexible conduit 21 after insertion into the trachea of a patient. An inflatable cuff 24C is positioned proximate the distal end 14C of the first flexible conduit 21. The inflatable cuff 24C includes a first 25A and second 25B end. The first end 25A of the inflatable cuff 24C is hermetically sealed about the periphery 26A of the first flexible conduit 21 proximate the distal end 14C. The second end 25B of the inflatable cuff 24C is hermetically sealed about the periphery 26B of the figure-eight configuration 35 comprising the first 21 and second 20C flexible conduit, described in greater detail below, to form a closed chamber 25. The inflatable cuff 24C must be large enough to contact and sealingly conform to the interior wall of the trachea 30.

The distal end 22C of the second flexible conduit 20C extends midway 23 into the inflatable cuff 24C for enhanced acoustic reception of the heart sounds from the inflatable cuff 24C. The distal end 22C of the second flexible conduit 20C includes a terminal end 27 defining an angular cut 29 to enhance the acoustic reception of the heart sounds acoustically transmitted from the interior tracheal wall 30 through the inflatable cuff 24C and into the acoustically separate second flexible conduit 20C. The inflatable cuff 24C may be inflated at a low pressure thereby minimizing injury to the internal walls of the trachea against which the cuff is pressured.

Positioned at the proximal end 19C of the second flexible conduit 20C is a three-way valve 100 with a first port 102, a second port 104, a third port 106 and a fourth port 107. Such valves 100 are known in the art. The first port 102 is connected to the proximal end 19C of the second flexible conduit 20C in a fluid tight manner. The second port 104 of the three-way valve 100 is connected to the means for permitting the pressurizing of the second flexible conduit 20C, such as a syringe 108. The third port 106 of the three-way valve 100 includes a valve means 110 which preserves pressure integrity in the second flexible conduit 20C by blocking port 104 upon rotation of the valve means 110. The valve means 110 opens and closes the second port 104 by having formed in its periphery a duct which upon rotation can either provide fluid and therefore acoustic communication or upon further rotation, block fluid and acoustic communication of port 104. The valve means 110 of the three-way valve 100 further includes a bore extending therethrough which permits fluid and acoustic communication from the third port 106 of the three-way valve 100 to conduit 109 which is in fluid and acoustic communication with an electromechanical transducer 112. The bore extending through the valve means 110 is preferably about 2.16 mm. The third port 106 of the three-way valve 100 is connected to the electromechanical transducer 112 to permit the monitoring of pressure variations within the second flexible conduit 20C and the closed chamber 25 of the inflatable cuff 24C. The electromechanical transducer 112 produces an electrical signal which is a function of the pressure variation within the second flexible conduit 20C and the closed chamber 25. The electrical signal is used as an input to an output means 116, as shown at FIG. 9.

FIG. 7 is a sectional view of the endotracheal cardiac monitor 10C of FIG. 6 taken on the line 7—7 illustrating the figure-eight configuration 35. The second flexible conduit 20C includes an internal 131 and an external 33 wall or surface. The first flexible conduit 21 extends along the exterior wall 33 of the second flexible conduit 20C to form a figure-eight configuration 35 in sectional view. The figure-eight configuration is manufactured by extending and attaching a portion of the external wall 33 of the second flexible conduit 20C to a portion external wall 43 of the first flexible conduit 21 to provide a generally figure-eight configuration 35 in sectional view. Other methods of manufacture, such as integral extrusion of the first 21 and second 20C flexible conduits with a figure-eight configuration 35, can also be used. The figure-eight configuration 35 acoustically separates and isolates the heart sounds present in the second flexible conduit 20C from the sounds of breathed air and anesthetic gases passing through the first flexible conduit 21 which defines the respiratory passage 42.

FIG. 8 is a sectional view of another embodiment of the invention illustrating the figure-eight configuration 35 of the acoustically separate first flexible conduit 21 and second flexible conduit 20C with the addition of sound deadening material 39 to further acoustically separate and isolate the second flexible conduit 20C from the breathing sounds proximate thereto. Addition of sound deadening matter also partially "rounds out" 41 the external configuration of the endotracheal cardiac monitor tube 10C to provide a contiguously smooth external surface which enhances the comfort factor to the patient. The sound deadening material 39 is of the same composition as that forming the first flexible conduit 21 and the second flexible conduit 20C or foamed plastic to enhance sound isolation.

FIG. 9 is a schematic view of the second flexible conduit 20C of the endotracheal cardiac monitor 10C connected to the first port 102 of the three-way valve 100, with a syringe 108 connected to the second port 104 of the three-way valve 100 and an electromechanical transducer 112 connected to the valve means 110 which provides a bore therethrough to the third port 106 of the three-way valve 100 to provide fluid and acoustic communication from the endotracheal cardiac monitor 10C to transducer 112. Syringe 108 pressurizes the closed chamber 25 of the inflatable cuff 24C, the second flexible conduit 20C, conduit 109 which connects to the nipple 113 of the electromechanical transducer 112, to enable the acoustic energy of the cardiac pulse to be sensed by the electromechanical transducer 112. The electromechanical transducer 112 is connected by an audio cable 114 to an output means 116 which is similar to output means 76, described. Fourth port 107 is sealed in a fluid tight manner. Optionally, a pressure gauge may be connected at port 107 to indicate the status of the pressure in the pressurized system. A gauge is useful where the endotracheal cardiac monitor is in an operable position for a long period, such as in a patient under intensive care and requiring a monitor. The pressurized system includes: inflatable cuff, second flexible conduit, three-way valve, duct of valve means and flexible conduit 109.

Figure 10:
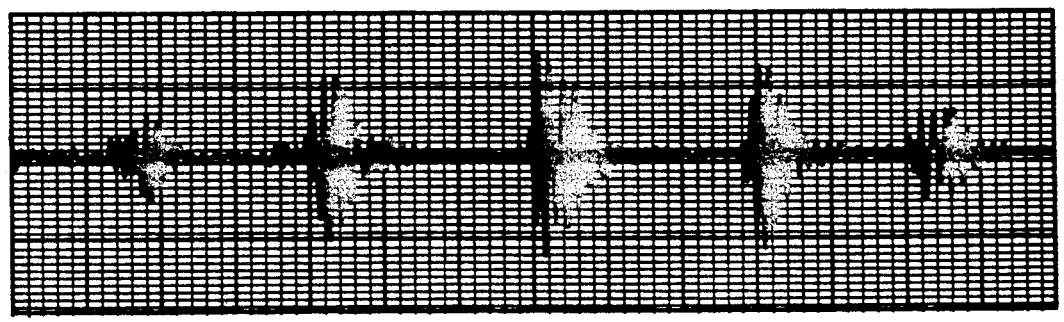
FIGS. 10 and 11 are graph comparisons of heart sounds.

FIG. 10 is a comparison of the heart sounds obtained by the use of a prior art device and by the use of the device of the instant invention.

COMPARATIVE EXAMPLE

An endotracheal cardiac monitor with a smaller tube bore, (second flexible conduit) of about 1 mm (prior art device) and an endotracheal cardiac monitor with a larger tube bore of about 2.16 mm (Applicant's device) are compared.

In the prior art device: the smaller tube of the prior art device exits the wall of the larger tube and is connected to and extends into a larger tube or bulb which is in turn connected to a coupling tube. The coupling tube in in turn connected to a coupling link. The coupling link is connected to a flexible tube which is connected to a three-way valve. The smaller tube terminates in the bulb prior to a portion of the coupling tube which intrudes into the bulb. The prior art device positions the smaller tube within the wall thickness of the larger tube beginning from within the inflatable cuff to a point about midway along the length of the larger tube, where the smaller tube exits. The smaller tube of the prior art device is provided with two apertures which enable fluid and acoustic communication with the interior of the inflatable cuff.

Applicant's device is of the structure described in the claims where the end of the second flexible conduit being directly connected to a three-way valve.

Figure 11:
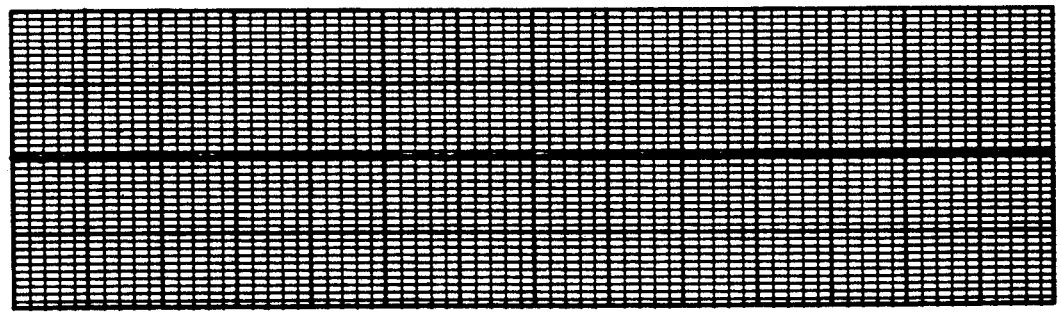

All connections in the prior art device and Applicant's device are made in a fluid tight manner. In each case the patient is first placed under general anesthesia. In each case the endotracheal cardiac monitor tube is positioned in the patient's trachea by standard procedure. In each case the proximal end of the smaller tube is connected directly to the transducer, i.e., absent any diaphragm. The cuff is then inflated by forcing air with a syringe to inflate the cuff to sealingly engage the wall of the trachea. To provide for connections between the smaller tube, the transducer and the syringe, a three-way valve is used. A valve means positioned in the three-way valve is manipulated to seal the port with the syringe attached thereto once the inflatable cuff is inflated. The valve means is modified by boring therethrough a duct to provide a substantially constant bore through the pressurized system. The transducer is directly connected to a signal processor. Head phones connected to an amplifier are used to ascertain heart sounds. The volume of the amplifier is increased until heart sounds, if any, are detected. The volume with the use of Applicant's device is set between 3 and 5. At this level, the prior art device did not evidence any discernible heart sounds and the level is increased to 8. At the above respective levels, a sound recording is made. The graphs set forth in FIGS. 10 and 11 are then generated at a later time from the sound recordings. As illustrated at FIG. 10, Applicant's device performed substantially better in obtaining heart sounds than the prior art device, FIG. 11.

The actual sound the heart makes indicates to one skilled in the art whether the gaseous anesthetic being administered to the patient is depressing the heart.

A preferred arrangement of the endotracheal tube 120 is shown in FIG. 12 where the first conduit 121 is shown formed by inner wall 131 and outer wall 130. Note that the thickness D of this structure is approximately 1.4 mm as shown in the chart below. This dimension is relatively constant over approximately three-quarters of the circumferential area of conduit 121 to define a first radial section of the conduit wall. In one area, the wall is flattened to define a chord 123 to give the interior conduit 121 an egg-shaped or elliptical profile. Adjacent to the chord 123, the wall thickness K is expanded to approximately 3 mm to define a second radial section of the conduit wall to accommodate the second conduit 122. The second conduit 122 has a diameter of approximately 2.16 mm and is separated from conduit 121 by a wall thickness G of approximately 2.0 mm. The peripheral area 126 surrounding the two conduits is substantially round for most of its circumference and expanded slightly in the area of 127 to accommodate the expanded side wall. This forms a smooth curve around the body of the endotracheal tube and, in reality, this expanded area is almost unnoticeable to the untrained eye.

Line 130A shows the continuation of the outer circumference of canal 121 if the second canal had not been formed. The expanded distance between line 130A and new outer circumference 127 is less than the diameter B of canal 122. This conserves space in the trachea while allowing maximum canal diameters for 2 canals.

Extending longitudinally along the endotracheal tube is a radio paque strip 129 which is used to monitor the position of the endotracheal tube during insertion and use of the tube.

It can be noted from the chart below that the diameter of conduit 121 is approximately 7.4 mm, while the diameter of conduit 122 is 2.16 mm, giving a ratio of approximately 3.5 to 1 between the two conduits. The 2.16 mm diameter of conduit 122 yields a sufficient cross-sectional area for acoustic waves to pass through the conduit uninhibited by the side walls and yet separated from conduit 121 acoustically to avoid interference while enhancing the ability of the endotracheal tube to preform the desired function thereby reducing even further the risks from surgery. It should be appreciated to those skilled in the art that the acoustical energy of an acoustical wave front propagating through conduit 122 is directed proportionally to the cross-sectional area of conduit 122.

| CHART C1 | |
| --- | --- |
| | Metric (mm) |
| A | 7.41 |
| B | 2.16 |
| C | 10.31 |
| D | 1.42 |
| E | 4.83 |
| F | 0.64 |
| G | 0.64 |
| H | 1.02 |
| J | 1.14 |
| K | 3.44 |

The advantages of the invention embraced in the second embodiment include an enhanced acoustic reception of the cardiac sounds passing from the inflatable cuff and through the second flexible member by providing a second flexible conduit which is acoustically isolated from the first flexible conduit and where the distal end of the second flexible conduit extends midway into the closed chamber of the inflatable cuff. Furthermore, the distal end of the second flexible conduit includes a terminal end which defines an angular cut to enhance the acoustic reception of the heart sounds acoustically transmitted from the interior tracheal wall through the inflatable cuff and into the acoustically separate second flexible conduit. In addition the axial bore of the second flexible conduit, the three-way valve ports, the valve means, and the conduit 109 connecting the electromechanical transducer to the third port 106 of the three-way valve are substantially the same size. A direct fluid tight coupling of the electromechanical transducer to the valve means positioned in the three-way valve is accomplished without the use of a diaphram 56 such as illustrated at FIG. 4. It should be appreciated by those skilled in the art that the overall diameter of the endotracheal tube 120 is limited by the size of the esophagus of a patient. Furthermore, the cross-sectional area of the first conduit 121 must be sufficient to allow proper respiration The present invention does not appreciably increase the overall diameter of the endotracheal tube 120 while simultaneously having a sufficient cross-sectional area in the first conduit 121 and an increased cross-sectional area in the second conduit 122. The increase in cross-sectional area of second conduit 122 increases the acoustical output of the heart sounds.

In use, as shown in FIG. 6, the cardiac pulse is transmitted by tissue and body fluids to the nearby trachea wall 30. Inflatable cuff 24C, in physical contact with the interior wall 30 of the trachea, acoustically couples the cardiac pulse to the fluid pressurization medium within inflatable cuff 24C. The cardiac pulse then propagates in the same pressurization medium from the vicinity of the inflatable cuff 24C through the hollow, communicating conduit 20C, three-way valve 100 to reach electro-mechanical transducer 112 which is connected in a fluid tight manner to the three-way valve 100. As shown in FIG. 9, the electromechanical transducer 112 connects with the third port 106 of the three-way valve 100. This alleviates the need for a diaphragm 56 (FIG. 3) which serves to maintain the pressure integrity of the inflation system. In this embodiment, the cardiac pulse is directly coupled acoustically to the acoustic monitor.

In use, the distal end 14 of endotracheal tube 12 is inserted through the mouth of the patient and into the trachea to the desired depth. Monitor connector 40 is attached to the desired acoustic or visual monitor and inflation connector 36 is attached to the anesthesia machine, not shown in the drawings, or other apparatus such as a syringe to provide fluid pressurization of inflatable cuff 24 through conduits 34 and 20. Although air is the most common pressurization medium, it will be appreciated by those skilled in the art that other fluid media, including liquids, may also be used for pressurization and to provide acoustic coupling. As the pressurization medium is pumped into the conduit through inflation connector 36, which often contains a check valve, the soft inflatable cuff 24 expands until it comes into contact with the interior wall 30 of the trachea. That point of contact typically is in the proximity of the heart.

The cardiac pulse is transmitted by tissue and body fluids to the nearby trachea wall 30. Inflatable cuff 24, in physical contact with the interior wall 30 of the trachea, acoustically couples the cardiac pulse to the fluid pressurization medium within inflatable cuff 24. The cardiac pulse then propagates in the same pressurization medium from the vicinity of the inflatable cuff 24 through the hollow, communicating conduit 20, tee 32 and conduit 38 to reach the monitor connector 40. The cardiac pulse is coupled acoustically with the desired acoustic or visual monitor.

As discussed above with respect to FIG. 5, the cardiac pulse may be displayed visually, as on an oscilloscope or a chart recorder, and the cardiac pulse may also be presented as an audio output which can be broadcast by means of a loudspeaker or which may be limited to the use of the anesthesiologist through the use of headphones as is well known in the art. The use of a loudspeaker, of course, enables the surgeon(s) to make an evaluation of the heart condition during surgery which is independent of that of the anesthesiologist.

The present disclosure includes that contained in the appended claims as well a that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A flexible endotracheal cardiac monitor for insertion into the trachea of the patient supplying life supporting and anesthetic gases to the patient and for acoustically monitoring actual heart sounds of the patient, comprising:

a flexible conduit defined by a conduit wall extending between a proximal end and a distal end;

said conduit wall of said flexible conduit having an internal surface and an external surface with said internal surface defining a first axial bore extending from said proximal end to said distal end of said flexible conduit;

said internal surface and said external surface of said flexible conduit defining therebetween a first radial section of said conduit wall and a second radial section of said conduit wall;

said first radial section of said conduit wall having a first conduit wall thickness and said second radial section of said conduit wall having a second conduit wall thickness;

a second axial bore being defined totally within said second radial section of said conduit wall and extends longitudinally along said first axial bore between a proximal end and a distal end;

said second axial bore being separated from said first axial bore by an inner conduit wall portion and being separated from said external surface of said flexible conduit by an outer conduit wall portion;

said second conduit wall thickness of said second radial section of said conduit wall comprising said inner conduit wall portion, said outer conduit wall portion and said second axial bore;

an inflatable cuff sealed to said external surface of said conduit wall and being positioned in proximity to said distal end of said flexible conduit;

said distal end of said second axial bore terminating within said inflatable cuff for enabling said inflatable cuff to be inflated to contact and sealingly conform to the interior wall of the trachea of the patient when pressure is applied to said proximal end of said second axial bore;

said first axial bore providing a respiratory passage for the administration of life supporting and anesthetic gases to the patient and for the control and monitoring of respiration of the patient during surgery;

said inflatable cuff receiving the actual heart sounds acoustically transmitted from the interior tracheal wall to enter said distal end of said second axial bore to propagate through said second axial bore and to be monitored at the proximal end thereof;

said inner wall portion of said conduit wall acoustically separating said first axial bore from said second axial bore to enhance the isolation of the acoustic heart sounds internal said second axial bore from the sounds of breathed air and anesthetic gases passing through said first axial bore;

said internal surface of said flexible conduit adjacent said first radial section of said conduit wall defining said first axial bore to be substantially circular in cross-section;

said internal surface of said flexible conduit adjacent said second radial section of said conduit wall defining a chord in cross-section intersecting with said substantially circular in cross-section adjacent said first radial section of said conduit wall; and each of said inner wall portion and said outer wall portion of said second radial section of said conduit wall being approximately one-half of the thickness of said first conduit wall thickness of said first radial section of said conduit wall for establishing said second axial bore to be sufficient in cross-sectional area to facilitate the propagation of the acoustic heart sounds through said second axial bore to the proximal end thereof without appreciably increasing the outer dimensions of said flexible conduit and without appreciably reducing the cross-sectional area of said first axial bore.

2. The flexible endotracheal cardiac monitor as set forth in claim 1, wherein said first axial bores has a diameter of approximately three times a diameter of said second axial bore.

3. The flexible endotracheal cardiac monitor as set forth in claim 2, wherein the diameter of said first axial bore has a diameter of approximately 7 mm; and said external surface of said flexible conduit has a diameter of approximately 10 mm.

4. The flexible endotracheal cardiac monitor as set forth in claim 1, wherein said external surface of said flexible conduit defines said first radial section of said flexible conduit to be substantially circular in cross-section;

said external surface of said flexible conduit defines said second radial section of said conduit to radially outwardly project beyond said substantially circular in cross-section of said first radial section of said flexible conduit;

and said chord of said internal surface radially inwardly projecting into said substantially circular in cross-section adjacent said first radial section of said conduit wall enabling said radially outwardly projection of said second radial section to project beyond said substantially circular in cross-section of said first radial section of said flexible conduit a distance less than the combined thickness of said inner and outer wall portions and a diameter of said second axial bore.

5. The flexible endotracheal cardiac monitor as set forth in claim 1, further including a three-way valve having a first port, a second port and a third port;

said first, second and third ports being in fluid communication with one another; and said proximal end of said second axial bore being connected to said first port of said three-way valve to enable fluid communication with said inflatable cuff.

6. The flexible endotracheal cardiac monitor as set forth in claim 5, wherein said second port of said three-way valve is connected to a means for pressurizing said inflatable cuff through said second axial bore.

7. The flexible endotracheal cardiac monitor as set forth in claim 6, wherein said second port of said three-way valve includes a valve means to maintain pressure integrity in said second axial bore while enabling acoustic communication through said third port of said three-way valve for receiving the heart sounds propagating from said proximal end of said second axial bore.

8. The flexible endotracheal cardiac monitor as set forth in claim 7, wherein said third port of said three-way valve is directly connected in a fluid tight manner to an electromechanical transducer to permit the direct monitoring of pressure variations within said second axial bore due to the heart sounds propagating from said proximal end of said second axial bore.

9. The flexible endotracheal cardiac monitor as set forth in claim 8, wherein said electromechanical transducer produces an electrical signal which is a function of said pressure variation; and said electrical signal is used as an input to an output means.

10. The flexible endotracheal cardiac monitor as set forth in claim 9, wherein said output means comprises a signal processor;

said signal processor performing amplification, filtering and impedance matching functions;

a visual display driven by said signal processor;

audio output means driven by said signal processor; and a chart recorder driven by said signal processor.

11. The flexible endotracheal cardiac monitor as set forth in claim 10, wherein said valve means positioned in said third port of said three-way valve includes a duct formed therethrough to enable fluid communication with an electromechanical transducer to permit the direct monitoring of said pressure variations within said second flexible conduit and said closed chamber of said inflatable cuff.

* * * * *